United States Patent [19]

Goel

[11] Patent Number: 4,623,744

[45] Date of Patent: Nov. 18, 1986

[54] PHOSPHOROUS CONTAINING DERIVATIVES OF BICYCLIC AMIDE ACETALS

[75] Inventor: Anil B. Goel, Worthington, Ohio

[73] Assignee: Ashland Oil, Inc., Russell, Ky.

[21] Appl. No.: 696,964

[22] Filed: Jan. 31, 1985

[51] Int. Cl.$^4$ ............................ C07F 9/46; C07F 9/30
[52] U.S. Cl. .................................... 558/170; 558/90; 558/95; 558/104

[58] Field of Search ...................... 260/972, 978, 944; 558/170, 90, 95, 104

Primary Examiner—Anton H. Sutto
Attorney, Agent, or Firm—John F. Jones

[57] ABSTRACT

A process for the preparation of novel phosphorous containing compounds by the reaction of bicyclic amide acetals with certain types of phosphorous compounds is disclosed.

15 Claims, No Drawings

PHOSPHOROUS CONTAINING DERIVATIVES OF BICYCLIC AMIDE ACETALS

This invention relates to novel phosphorous containing derivatives of bicyclic amide acetals and to a process for their preparation.

Bicyclic amide acetals and bis bicyclic amide acetals are relatively new materials. The preparation of some of the bicyclic amide acetals is more fully disclosed in the copending U.S. patent applications of Anil B. Goel and of Anil B. Goel and Harvey J. Richards, respectively, filed as Ser. Nos. 641,238 and 641,242 on Aug. 16, 1984.

I have discovered that bicyclic amide acetals and bis bicyclic amide acetals as more fully described below will react with certain phosphorous compounds as more fully described below to form new compounds more fully described below which have utility as ligands, monomers and in polymers, particularly of the condensation type.

The bicyclic amide acetals and bis bicyclic amide acetals useful in this invention include those conforming to the Formulas I and II.

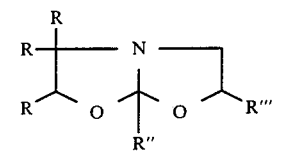

I

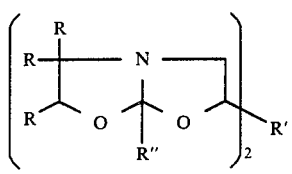

II

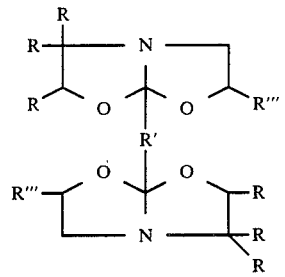

III

Wherein R independently represents hydrogen or an alkyl group having from 1 to 18 carbon atoms, R' represents an alkylene group having from 1 to 18 carbon atoms, a cycloalkylene group having from 6 to 18 carbon atoms, or an arylene group having from 6 to 12, carbon atoms or an ether having from 2 to 18 carbon atoms, R" represents hydrogen, an alkyl group having from 1 to 18 carbon atoms, or an alkaryl or aryl group having from 6 to 18 carbon atoms, and R''' represents hydrogen or an alkyl group having from 1 to 18 carbon atoms or an aryl or alkaryl group having from 6 to 18 carbon atoms or an ether group having from 1 to 18 carbon atoms.

The phosphorous compounds useful in this invention include those conforming to the following Formulas IV, V and VI.

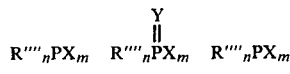

Wherein the phosphorous is trivalent in Formula IV, R'''' represents hydrogen or hydrocarbon, an oxyhydrocarbon or ester group having 1 or more carbon atoms, X represents a halogen, an hydroxyl group or a thiol group, n represents a number from 0 to 2, m represents a number from 1 to 3 and the sum of n+m is always 3. The Formula V phosphorous is pentavalent and R'''' has the foregoing designation, Y represents oxygen, sulfur or NH and n and m have the foregoing designations. In Formula VI phosphorous is pentavalent, R'''' and X have the foregoing designations, n is a number from 0 to 4, m is a number from 1 to 5 and the sum of n+m is always 5.

To illustrate the process of this invention, the reaction of a bicyclic amide acetal of Formula I with a phosphorous compound of Formula IV in which n is 2 and m is 1 is shown in the following equation:

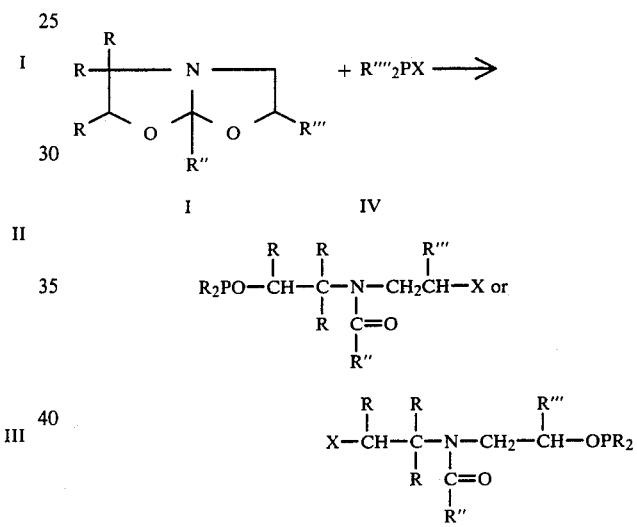

Wherein R, R", R''', R'''' and X have the foregoing designations.

The process of this invention can be carried out conveniently at temperatures in the range of from about room temperature up to about 200° C. or higher at pressures in the range of from about atmospheric or below up to about 100 atmospheres. It is usually most convenient to carry out the process at about room temperature and about atmospheric pressure.

This invention is further illustrated in the following representative Examples.

EXAMPLE 1

To 25.8 g of a bicyclic amide acetal of Formula I in which R and R''' represent hydrogen and R" represents methyl were added 8.2 g of phosphorous acid and the resulting mixture was stirred at room temperature. An exothermic reaction took place in about two minutes. The resulting mixture was stirred at 80° C. for one hour to give a viscous liquid product. Infrared analysis of this liquid showed the presence of a product having hydroxyl, amide and phosphorous ester groups and having the formula

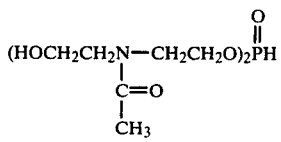

EXAMPLE 2

To 13 g of the bicyclic amide acetal described in Example 1 was added dropwise 9 g of phenyl dichloro phosphine (PhCl$_2$). An exothermic reaction occurred at room temperature. The resulting viscous liquid was stirred at 60° C. for one hour to complete the reaction. Infrared analysis of the product showed that it contained primarily

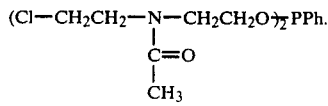

EXAMPLE 3

Chloro (diphenyl) phosphine (Ph$_2$PCl,11 g) was added dropwise with stirring to 6.5 g of the bicyclic amide acetal described in Example 1 at room temperature. An exothermic reaction occurred. After completion of the addition, the stirred reaction mixture was allowed to react further at 60° C. for one hour to give a liquid product which was found by infrared analysis to have the structure

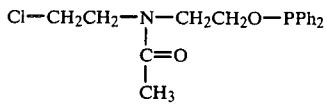

This product was found to be useful as a ligand for transition metals. When 3.5 g of the product was added to a solution of 1.12 g of palladium acetate in 50 ml of benzene, the mixture was stirred at room temperature for 3 hours and the benzene was then stripped off a solid orange-red palladium complex product resulted.

EXAMPLE 4

A mixture of 1.38 g of phosphorous trichloride and 2.6 g of the bicyclic amide acetal described in Example 1 was stirred at room temperature. An exothermic reaction took place producing a product which was identified by infrared analysis as

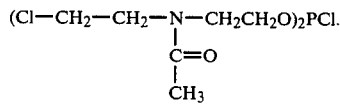

EXAMPLE 5

A bis bicyclic amide acetal of Formula II in which R is hydrogen, R" is ethyl and R' is ethylene (3.45 g) and 0.83 g of phosphorous acid (H$_3$PO$_3$) were mixed and heated at 100° C. for one hour. An orange-red polymeric material which was found to be soluble in water resulted. The solid, thermoplastic polymeric product was found to have good adhesion to metals such as steel and aluminum with bond strengths greater than 200 psi.

EXAMPLE 6

A mixture of 3.2 g of phenyl phosphonic acid

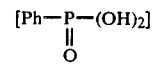

and 5.2 g of the bicyclic amide acetal described in Example 1 was stirred and heated at about 90° C. for two hours. The resulting product was shown by infrared analysis to be

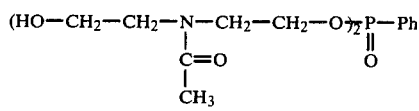

EXAMPLE 7

A mixture of 8.7 g of phosphorous acid (H$_3$PO$_3$) and 65 g of the bicyclic amide acetal of Example 1 was stirred and heated at 70° C. for one hour. The resulting product was found to be the product of Example I. The product was degassed and was mixed with 145 g of degassed, liquid 4,4'-methylene bis(phenyl isocyanate) and the mixture was poured into a mold formed from parallel glass plates which were coated with a silicone mold release agent and were spaced ⅛" apart. The sheet thus formed was cured at 100° C. for one hour and then for another two hours at 135° C. The resulting solid polymer sheet was found to have an ASTM D-648 heat distortion temperature of 148° C. and an ASTM D256 notched IZOD impact strength of 0.45 foot pounds/inch of notch.

EXAMPLE 8

A bicyclic amide acetal of Formula I in which R and R''' are hydrogen and R" is a methyl group (2.5 g) was added to 400 ml of dry toluene and to this solution was added 40 g of phosphonylated polypropylene (polypropylene having about 0.2% by weight of

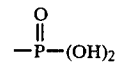

groups on the polymer chains). The resulting slurry mixture was stirred and heated at 70° C. under a nitrogen atmosphere for 5 hours and the toluene solution was analyzed from time to time during this reaction. GC analysis showed that some of the bicyclic amide acetal disappeared from the solution during the reaction and reacted with the solid polymer. At the end of the reaction period, the reaction mixture was cooled and the polymer was isolated by reduced pressure filtration. The adhesive properties of the polymer product were tested by melting some of the polymer at 150°–200° C. and placing the melt between both aluminum and cold rolled steel sheets with one square inch of overlap. The bond line thickness was about 30 mils. The shear strengths were tested and adhesive failure was found to be between 600 and 660 psi in each case.

EXAMPLE 9

The procedure of Example 8 was repeated using 5 g of phosphonylated polypropylene containing

groups in the polymer, 0.4 g of bicyclic amide acetal and 50 g of toluene. The aluminum adhesion test for the polymer product gave a shear strength of about 750° psi.

I claim:

1. The process for preparing phosphorous derivatives of bicyclic amide acetals comprising reacting a bicyclic amide acetal conforming to the Formula I, II, or III

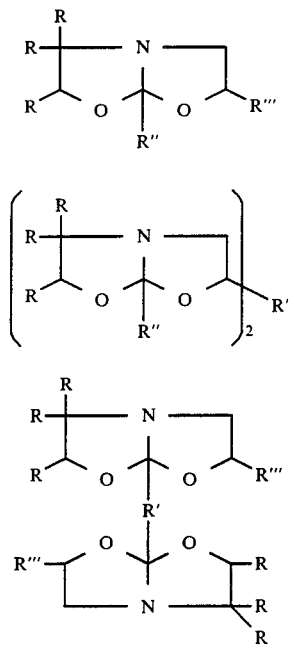

wherein R independently represents hydrogen or an alkyl group having from 1 to 18 carbon atoms, R' represents an alkylene group having from 1 to 18 carbon atoms, a cycloalkylene group having from 6 to 18 carbon atoms or an arylene group having from 6 to 12 carbon atoms or an ether having from 2 to 18 carbon atoms, R" represents hydrogen, an alkyl group having from 1 to 18 carbon atoms or an alkaryl or aryl group having from 6 to 18 carbon atoms, and R''' represents hydrogen or an alkyl group having from 1 to 18 carbon atoms or an aryl or alkaryl group having from 6 to 18 carbon atoms or an ether group having from 1 to 18 carbon atoms with a phosphorous compound conforming to Formula IV, V or VI.

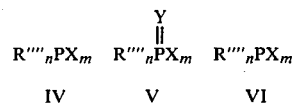

wherein the phosphorous is trivalent in Formula IV, R'''' represents hydrogen or a hydrocarbon, an oxyhydrocarbon or ester group having 1 or more carbon atoms, X represents a halogen, an hydroxyl group or a thiol group, n represents a number from 0 to 2, m represents a number from 1 to 3 and the sum of $n+m$ is 3; in Formula V phosphorous is pentavalent, R'''' has the foregoing designation, Y represents oxygen, sulfur or NH and n and m have the same designations as in Formula III; in Formula VI phosphorous is pentavalent, R'''' and X have the foregoing designations, n is a number from 0 to 4, m is a number from 1 to 5 and the sum of $n+m$ is 5.

2. The process of claim 1 carried out at a temperature in the range of from about room temperature up to about 200° C.

3. The process of claim 2 carried out at a pressure in the range of from about atmospheric up to about 100 atmospheres.

4. The process of claim 3 wherein the bicyclic amide acetal is one having Formula I in which R and R''' are hydrogen and R" is methyl.

5. The process of claim 3 wherein the bis bicyclic amide acetal is one having Formula II in which R is hydrogen, R" is ethyl and R' is ethylene.

6. The process of claim 4 wherein the phosphorous compound is phosphorous acid.

7. The process of claim 4 wherein the phosphorous compound is phenyl dichloro phosphine.

8. The process of claim 4 wherein the phosphorous compound is chloro(diphenyl) phosphine.

9. The process of claim 4 wherein the phosphorous compound is phosphorous trichloride.

10. The process of claim 5 wherein the phosphorous compound is phosphorous acid.

11. The process of claim 4 wherein the phosphorous compound is phenyl phosphonic acid.

12. The process of claim 4 wherein the phosphorous compound is phosphoric acid.

13. The process of claim 4 wherein the phosphorous compound is a phosphonylated polypropylene.

14. The composition produced by the process of claim 1.

15. The composition produced by the process of claim 3.

* * * * *